United States Patent [19]

Olive

[11] Patent Number: 5,049,141
[45] Date of Patent: Sep. 17, 1991

[54] PROGRAMMABLE VALVE PUMP

[75] Inventor: Peter Olive, Needham, Mass.

[73] Assignee: Infusaid, Inc., Norwood, Mass.

[21] Appl. No.: 514,442

[22] Filed: Apr. 25, 1990

[51] Int. Cl.$^5$ .............................................. A61M 31/00
[52] U.S. Cl. ......................... 604/891.1; 128/DIG. 12; 604/118
[58] Field of Search ............... 604/118, 131, 141, 142, 604/246, 891.1; 417/412, 413; 128/DIG. 12, DIG. 13

[56] References Cited

U.S. PATENT DOCUMENTS

| | | | |
|---|---|---|---|
| 4,221,219 | 9/1980 | Tucker | 604/141 |
| 4,303,376 | 12/1981 | Siekmann | 604/141 |
| 4,515,588 | 5/1985 | Amendolia | 604/118 |
| 4,714,462 | 12/1987 | Didomenico | 604/891.1 |
| 4,838,887 | 6/1989 | Idriss | 128/DIG. 12 |
| 4,936,758 | 6/1990 | Coble | 417/413 |

Primary Examiner—Cary E. Stone
Assistant Examiner—Michael Lynch
Attorney, Agent, or Firm—Sughrue, Mion, Zinn, Macpeak & Seas

[57] ABSTRACT

An implantable valve accumulator pump for the delivery of medication is disclosed. The implantable pump comprises a drug reservoir maintained at constant pressure vapor. The medication metering assembly comprises a fixed volume accumulator positioned between a pair of valves. The valves alternately open and close to admit medication from the reservoir into the accumulator and to dispense a precise volume spike to an outlet catheter. In order to minimize dead volume and insure complete discharge, the accumulator employs a titanium diaphragm seated in one position by a recessed stop and in the discharge position by a spacer plate having a concentric groove pattern. The grooves are in fluid communication with the inlet and outlet. Also, a wide groove extending between inlet and outlet provides fluid communication between the grooves. The unit is externally programmed.

28 Claims, 4 Drawing Sheets

PROGRAMMABLE VALVE PUMP

BACKGROUND OF THE INVENTION

This invention relates to an implantable infusion pump for the dispensing of infusate. In particular, it relates to a pump operating at positive pressure which is programmable to dispense medication in accordance with different specified flow rates. This invention is directed at improving the operation of a valve accumulator in such a system.

Implantable infusion pumps are currently used for a variety of medical purposes. Typical of such commercially acceptable devices are the INFUSAID Model 100 and 400 devices. Such devices are implantable in the human body and rely on a liquid/vapor equilibrium to maintain constant pressure on the drug which is housed therein so that the drug flows through a capillary in order to maintain a constant flow rate. Such devices are characterized by "constant flow" and are used in a variety of medical applications, for example, to dispense chemotherapy at a relatively constant flow rate. As background to the INFUSAID Model 100 and 400 devices, are U.S. Pat. Nos. 3,731,681 and 4,496,343.

There are a variety of medical conditions where a patient requires an adjustment in the dosage and as such, constant flow pumps are inadequate. A typical example is diabetes where the quantity of medication, such as insulin, to be infused varies due to requirements of the patient. Fluctuations can occur on a daily basis or more randomly as a function of the ingestion of food. It is known that the amount of medication to be infused per unit of time should be adjusted at certain time intervals. A patients requirements may fluctuate at either set, known rates or vary abnormally, for example, by the ingestion of food or other transitory conditions. Those conditions require the administration of a bolus dose of infusate. The daily administration of insulin requires a basal dose that is supplanted by bolus doses, for example, at meal times. The difference in flow rates between the basal and bolus doses may be quite large, the bolus dose several orders of magnitude larger than the basal dose. Consequently, to achieve proper flow rates over the spectrum of desired rates, such a device must have the ability to continually infuse at very low rates yet provide, periodically a substantially increased flow rate.

Within the reported literature, a number of implantable programmable concepts have been disclosed. Typical are U.S. Pat. Nos. 3,894,538; 4,077,405; and 4,443,218. A category of programmable pumps is so-called negative pressure pumps typified by U.S. Pat. Nos. 4,482,346 and 4,486,190. These devices are solenoid activated negative pressure devices. In those systems a diaphragm storage chamber maintains the drug to be infused. A diaphragm separates the drug from propellant, normally Freon maintained at negative pressure. The solenoid is activated driving an armature and a bellows pumping element. The displacement of the armature opens a check valve which draws drug from the storage chamber into a downstream pumping chamber. A restriction is used to prevent backflow in the outlet during this short period. When the pump chamber is full, the check valve closes and the solenoid is deenergized. A spring force is used to displace the bellows into the chamber thereby pumping the drug through a restrictor and into the patient. The bellows armature assembly comes to rest on the check valve to insure that no backflow occurs during the rest period. Such a system operates at negative pressure to insure no forward flow during this rest period, that is the drug chamber pressure is below body pressure.

Such negative pressure systems suffer from several significant disadvantages. First, the ingestion of air into the system will stop the drug flow process. Consequently, such devices require expensive fill and empty systems for recycling of the implantable device. A more practical and serious problem is that special handling is required for the devices themselves. The drugs used with such devices must be vacuum conditioned thereby requiring that special steps be taken by those who in many cases are medical technicians and are technically unsophisticated. The drugs must also be packaged and shipped with special care to maintain such vacuum conditioning. Consequently, these devices, while offering theoretical advantages, in practice suffer from significant disadvantages.

A second class of device is the so-called positive pressure pumps which are used in combination with an accumulator pump. Typical are U.S. Pat. Nos. 4,221,219; 4,299,220; and 4,447,224. Such devices operate at positive pressure thereby eliminating the problems of prior art negative pressure devices. Because the drug chamber is maintained above body pressure, there is, however, a remote potential for an overdose of drug should all the valves inline with the output fall open at the same time. An extremely high degree of safety, however, may be achieved in such systems by the use of redundant or fail-safe valves together with the addition of sensor/shut-down circuits. Such, however, results in significant cost increases which are added to the system.

Reference is made to U.S. Pat. No. 4,525,165. This patent employs a series of pump and accumulator elements between the drug chamber and the outlet. Medication is drawn out of the chamber by a pump and delivered to a bellows accumulator. This system is not only complex but cannot accurately meter doses given the variable volume of the bellows.

To deal with these situations where deficiencies exist within prior art devices. U.S. Pat. No. 4,714,462, commonly assigned, deals specifically with a programmable positive displacement system having a pumping chamber which is placed in the path of fluid communication between the pressurized drug reservoir and a flow restrictor. By use of external programming, the device can be used to expel infusate from the pumping chamber at varying rates. While such systems provide advantages over the prior art, a need exists to define a system which is simple in operation yet provides the ability to accurately meter dosage. System simplification by the elimination of bellows chambers, implantable solenoids and the like with their attendant power requirements, represent a standing requirement for reliability and ease of operation of such implantable devices.

While not implantable devices, there exists in separate art, techniques for dispensing fluids by intravenous administration. Representative are U.S. Pat. Nos. 4,121,584; 4,261,356 and 4,262,824. These devices employ a valved accumulator metering system from a hydrostatic source using a gravity feed. The problems inherent in implantable technology are not recognized or addressed. There is similarity in the concept of using a metering chamber that is valved as in the case of the '219 patent with a diaphragm, but the application to implantable devices is not stated nor recognized in the industry.

Reference is made to commonly assigned U.S. Pat. No. 4,838,887. This patent describes a programmable valve pump overcoming many of the problems of the prior art. The pump employs an accumulator having a spacer plate with a series of orthogonal checkerboard grooves. This is illustrated in FIG. 5B of the '887 patent. While suitable for a number of applications, it has been found that this spacer plate configuration allows the build-up of certain drug precipitation. The build-up of precipitation in turn reduces the pulse volume of the system thus reducing efficiency and accuracy of output dosage.

It has also been discovered that air bubbles can become trapped in the cross grooves of a gridded accumulator which as illustrated in the '887 patent are at right angles to the direction of the fluid flow. This occurs because there is no wash-out of the spacer. For the same reason, small particles can be trapped between the gridded spacer plate and the diaphragm. This causes a shift in pulse volume.

The gridded spacer plate is expensive to manufacture. It requires machining steps of turning and milling. The grid pattern in then chemically etched in the spacer plate.

SUMMARY OF THE INVENTION

This invention is a direct improvement over the technology of the '887 patent.

Given these recognized shortcomings in the prior art, it is an object of this invention to provide a positive pressure programmable valve pump that is implantable into a living body which is inexpensive and easy to manufacture.

It is a further object of this invention to define a system which utilizes a valved accumulator device to precisely deliver small quantities of a drug at programmed rates. Specifically, it is an object of this invention to define an improved accumulator system offering improved air and particle susceptibility. Consequently, reliability and simplicity of the system is a primary aspect of this invention.

It is a further object of this invention to define a device which operates using a wide variety of drugs without problems of internal build-up and specifically precipitation build-up on the accumulator spacer plate.

This invention comprises four essential components. The first is a rechargeable, positive pressure drug reservoir in series with a bacteria/air filter. The second major assembly is an electronically controlled metering assembly comprising two normally closed valves adjacent and opposite to a fixed volume accumulator.

This invention employs an improved accumulator configuration. Specifically, the accumulator is a concentric groove configuration having a number of sharp ridges created between adjacent grooves. The ridges support the drug side of the diaphragm when the accumulator is at the empty portion of the delivery cycle. This significantly reduces the contact area between the diaphragm and the spacer plate. In turn the surface pressure of the drug at the contact points increases to prevent accumulation of drug residue.

The third fundamental component used in the system is an outlet catheter. These three components comprise the implantable aspect of the pump. The fourth aspect of this invention is the external programmer.

In accordance with this invention, initial "pumping" is provided by the reservoir which is used to fill the accumulator to its fixed volume. The accumulator is then "dumped" via the discharge catheter to the desired infusion site. In accordance with this invention, a pressure which is intermediate between the reservoir and the outlet is maintained behind the accumulator so that it fills and empties completely and rapidly. The accumulator is alternately filled and emptied by the alternate switching of the valves. The rate of switching therefore governs the rate of pumping and thus the delivery rate.

Valve control is provided in the implantable pump by means of an on-board processing system and power supply. The processor is externally accessed through a telemetry link which can be used to both program the pump operation and obtain diagnostic information as to the operation of the device.

In accordance with basic implantable pump technology the pump reservoir may be refilled periodically and can be accessed transcutaneously by means of the reservoir septum. That is, in accordance with known techniques, a stressed elastomeric seal may be punctured with a specially shaped needle. The septum is self sealing for a defined number of punctures. Reservoir pressure is provided by a moderately high vapor pressure fluid in a twophase equilibrium. Such is known in the context of existing constant flow implantable devices. Pressure is recharged at each refill since the vapor is recondensed.

DESCRIPTION OF THE PREFERRED EMBODIMENT

Figure 1:
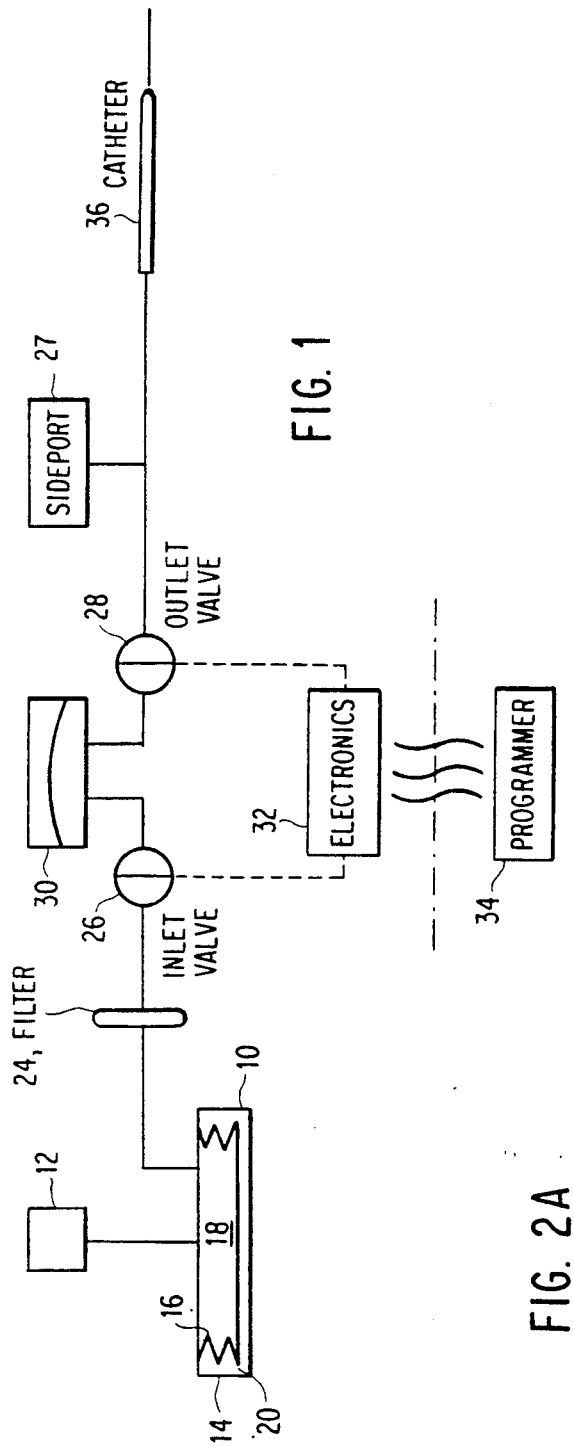
FIG. 1 is a schematic diagram showing the complete system and a schematic diagram of the flow.

Referring now to FIG. 1, schematic diagram of the essential aspects of this invention is depicted. The invention is a positive pressure programmable valve pump comprising a constant pressure drug reservoir 10 which is refillable by means of a septum 12. Such devices are known, for example, the INFUSAID Model 100 and 400 devices. Those systems comprise a sealed housing 14 containing a bellows element 16 having a chamber 18 comprising the drug reservoir. The bellows 16 separates the housing into a second zone 20 normally filled with a two-phase fluid which has a significant vapor pressure at body temperature. Thus, as the fluid vaporizes, it compresses the bellows 16 and urges the contents of the reservoir 18 through an outlet leading to an infusion site. During the process of refilling, the chamber 18 via the septum 12, the two-phase fluid is pressurized condensing a portion of the vapor and returning it to its liquid phase. As indicated, such basic constant pressure devices are known in the art as described in U.S. Pat. Nos. 3,731,681 and 4,221,219.

Typically, the reservoir 18 has a volume of approximately 25 ml and the pressurization maintained in the system is approximately 23.2 psia. In this invention however, there is no firm requirement for a constant pressure reservoir. The use of an accumulator will result in nearly a uniform metering over a wide range of reservoir pressures. Thus, gases other than Freon can be used. A sideport 27 can be used for direct bolus injections. Sideports are used in the INFUSAID Model 400 and described in U.S. Pat. No. 4,496,343.

An outlet 22, from the reservoir 18 delivers infusate from the reservoir via a bacterial filter 24 to the electronically controlled metering assembly.

The metering assembly comprises two normally closed valves 26, 28, which are positioned on the inlet and outlet sides of an accumulator 30. The accumulator operates at a constant volume, very low, in the range of 1 $\mu$l pressurized typically to 19.2 psia. The valves 26 and 28 are controlled electronically via a module 32 which is programmed utilizing an external programmer 34. FIG. 1 illustrated in a chain line, the pump envelope which separates the electronics 32, that is the system which is implanted, from the external programmer 34. The programmer can employ known technology for example that disclosed in the above co-pending application which is incorporated herein by reference.

The programmer 34 is a hand held unit using a touch screen. It provides a data transfer link to the electronics 32 implanted as a part of the device (see FIG. 3). In a memory, the programmer 34 maintains a patient history based on storage of real time data. Data as to device status, such as battery condition, diagnostics on valve current, prescription in use and the like are retained. The external programmer also has different interrogation modes such as initial calibration and protected modes for technician use.

The outlet from the accumulator 30 is via a catheter 36 which delivers the infusate to the site in the body to which drug delivery is required. As indicated by the arrow in FIG. 1, the delivery of infusate occurs at the infusion site below the accumulator pressure forcing discharge through the catheter. This pressure may be atmospheric (typically 14.7 psia) or cardiovascular pressures slightly above atmospheric, e.g. 17.6 psia arterial.

Figure 2B:
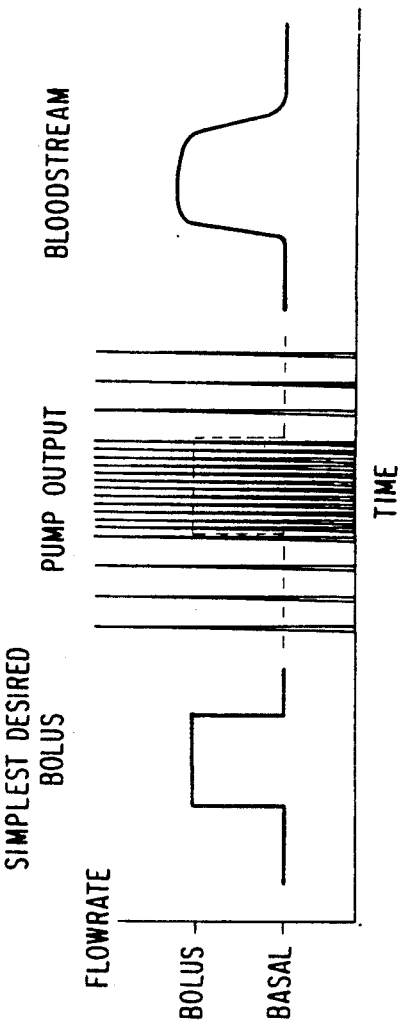
FIG. 2B is a time-flow rate chart of the delivery schedule of the system.
Figure 2A:
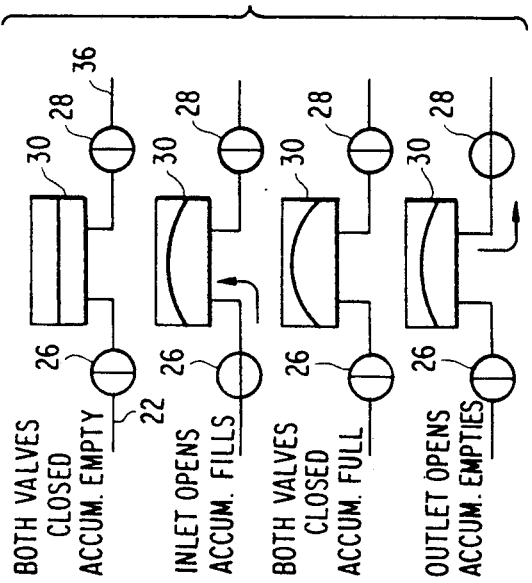
FIG. 2A is a schematic diagram illustrating the pumping cycle of the accumulator.

Referring now to FIG. 2A, the pumping cycle is schematically illustrated. The salient aspects of this section of the system comprise the valves 26, 28 and the accumulator 30. The first step is one where both valves 26 and 28 are closed and the accumulator 30 is empty. The drug is delivered from the reservoir 18 through conduit 22 and filter 24 to fill the accumulator 30. Thus, as a second step in the operation the valve 26 is opened while valve 28 is closed to fill the accumulator to its fixed volume. The third step is then to close both valves 26 and 28 with the accumulator now full. The final step in the accumulator cycle is the opening of valve 28 while valve 26 remains closed to empty the accumulator through the catheter 36. Consequently, the accumulator is alternately filled and emptied by the switching action of the valves. A pressure intermediate between that of the reservoir and the outlet is maintained behind the accumulator so that it fills and empties completely and rapidly. The rate of switching of the valves therefore governs the rate of pumping and accordingly determines the delivery rate of infusate.

Referring to FIG. 2B an example of the delivery rate of this system is illustrated. FIG. 2B is a chart plotting a flow rate in the y-axis against time in the x-axis. The output of the pump is periodic and is a function of the frequency of the valve cycle. Thus, the faster the valve cycle, the greater the number of accumulator discharges per unit. Each discharge is in the form of a volume spike.

In FIG. 2B a change from a basal rate to a desired bolus rate, that is an increase in flow rate above the basal rate, is illustrated by means of the square wave on the left-hand portion of the time chart. This would be the programmed bolus flow into the electronics package 32. The pump, to establish the required bolus flow rate, would increase the frequency of the discharge spikes by varying its pump cycle during the bolus period as illustrated in the center of FIG. 2B. The total number of spikes are integrated over time so that the flow rate volume replicates that required by the desired bolus flow rate. The output through the catheter 36 to the bloodstream is illustrated in the righthand portion of FIG. 2B.

By integrating the volume of the pump over time, given the number of pump cycles, and the volume of each discharge. digital basal and bolus rates closely replicating the required values, that is flow rates having the required amplitude over the required time, are delivered. With sufficiently chosen accumulator volume, drug concentration and discharge rate, the delivery site can filter the output to achieve a desired "continuous" and basal dosage.

Figure 3:
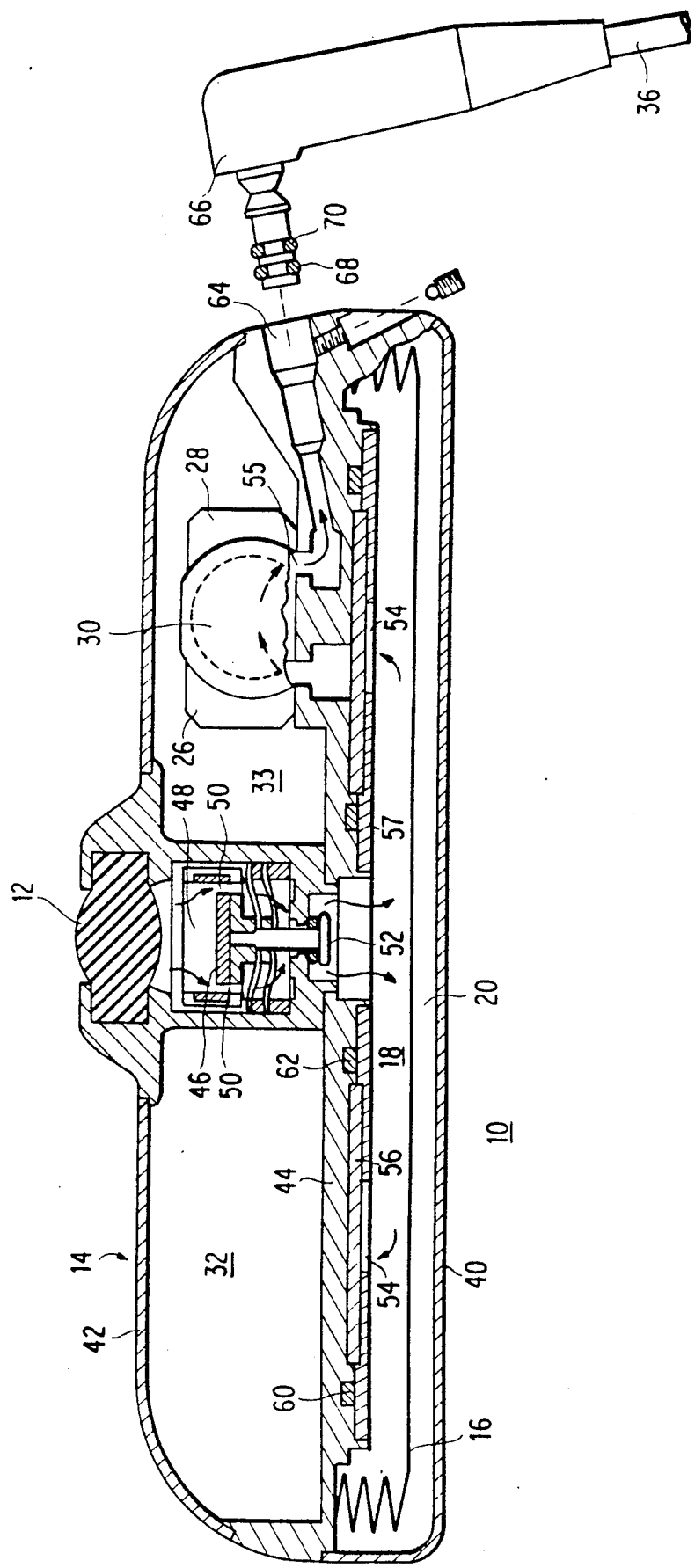
FIG. 3 is a cutaway side elevation of the basic construction of the implantable pump portion of the system.

Referring now to FIG. 3, the implantable portion of the system is illustrated in cross section. The implantable portion of the reservoir system 10 comprises a housing 14 having therein all of the essential elements comprising the reservoir 18, the Freon twophase pressurizing chamber 20, the electronics module in location 32, and the accumulator valve aspects of the system housed in location 33. The pump reservoir 18 is periodically accessed transcutaneously via the reservoir septum 12. The septum is a stressed elastomer seal which may be punctured with a specifically shaped needle. It is self-sealing for a finite number of punctures. As in the case of known systems, reservoir pressure is provided by a moderately high vapor pressure fluid maintained in a two-phase equilibrium. Freon is, as mentioned, a typical material. Pressure in the system is recharged with each refill since the Freon vapor is recondensed.

As illustrated in FIG. 3, the mechanical construction of the device comprises a hollow disk-shaped housing generally made of two components. That is, the housing 14 comprises a lower section 40 and an upper or cover section 42. The two main cavities of the system are separated by a solid base plate 44 which defines the central core of the unit. The lower cavity is subdivided into two chambers 18 and 20 by means of the bellows 16. Chamber 18 contains the drug while Chamber 20 contains the Freon pressurization system. During manufacture, a relatively small amount of the volatile fluid, typically Freon, is injected into the region 20 via a small fill tube not illustrated. The Freon then comes to a two-phase equilibrium within this chamber. The vapor pressure is determined by the equilibrium pressure and remains constant for constant pump temperature and quasi-static volume changes of the bellows 16. The magnitude of the storage reservoir pressure is then the sum of this vapor pressure and the mechanical pressure which is associated with the spring rate of the bellows 16.

The central core region contains the needle piercing septum through which drug is injected into the chamber 18. The septum includes a needle-stop 46. The needle-stop is a non-metallic cup which is used to support the needle and limit its travel yet at the same time prevent damage to the needle tip. When the needle is removed, drug is sealed in the reservoir 18.

Thus, the needle, not illustrated, punctures the septum 12 and comes to rest on the stop 46. Drug is then dispensed into chamber 48 and via flow passages 50, is delivered into the reservoir 18. A check valve 52 may optionally be used in the inlet. Thus, as illustrated by the flow arrows in FIG. 3, drug delivered into the chamber 48 passes through the through-holes 50 and, if in place the increased pressure of the fluid or the force of the needle pushing down on the needle stop 46 opens the check valve 52 to deliver drug into the chamber 18.

The system includes within the housing 14, the electronics cavity 32 containing the necessary microprocessor electronics and battery. Battery life is sufficient to power the device during its normal intended implantable life. The housing 14 includes within the central core region the two valves 26 and 28 and the accumulator 30. The valves 26 and 28 comprise two miniature solenoid valves which are intimately connected to the accumulator 30. The valves 26 and 28, to be discussed herein are manufactured by Wilson Greatbatch Company and illustrated in detail in FIG. 4. It is to be understood that such valves are commercially available. The valves hermetically isolate the fluid sides of the valve from the electrical side of the valve.

FIG. 3 illustrates by arrows the flow configuration from the chamber 18 to the outlet catheter 36. The drug, from chamber 18, passes through circular openings 54 through the annular filter assembly 56. The filter 56 is interposed between the base plate 44 and a backing plate 58 and is sealed at its radially inward and outward points by means of annular seals 60 and 62. The drug then passing through the filter 56 is subject to valve action by valve 26 filling the accumulator 30 and then dumped via valve 28 into the outlet port 64. A right angle connector 66, locked into the outlet port and sealed via O-rings 68 and 70, couples the housing 14 to the catheter 36.

Figure 4:
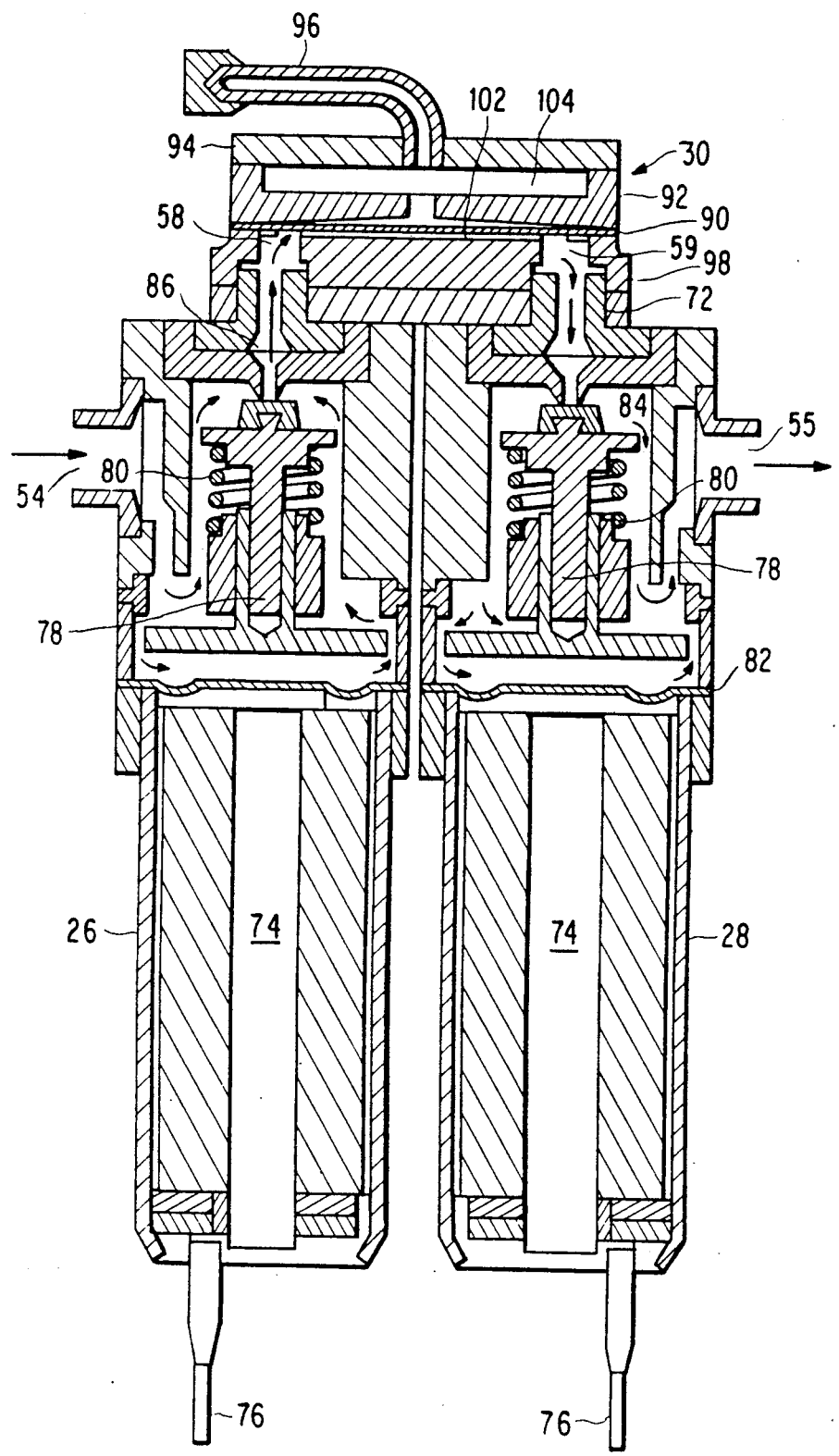
FIG. 4 is a cutaway schematic view of the valve/accumulator metering system in accordance with this invention.

Referring now to FIG. 4, the details of the valve/accumulator metering assembly are depicted. Valves 26 and 28 are miniature solenoid valves attached to the accumulator 30 by means of a weld point 72. Valves are disposed in a side-by-side arrangement having solenoid assemblies 74 and applicable input power via leads 76. The valves are operably powered to drive a working plunger 78 biased by means of spring 80. The working plunger and return spring assembly are isolated from the solenoids by means of an isolation diaphragm 82. This isolation diaphragm is a welded metal diaphragm sandwiched between both sides, that is the electrical side and the fluid side of the system. The diaphragm 82 does not transmit pressure to the working plunger 78 therefore the only pressure differential which opposes valve motion is that which is across the valve seat area.

The flow path is illustrated by the arrows in FIG. 4. At the input conduit 54, the nominal pressure of the infusate is 23.2 psia. With valve 26 in the open position, drug is delivered upward through the valve seat 84 (shown closed in FIG. 4), into the accumulator flow passage 86. As can be seen from FIG. 4, the configuration minimizes the total volume and any possible stagnant flow passages which exist between the valve seats. The area between the valve seats comprises the accumulator storage space. Consequently, to minimize entrapped air, a low "dead volume" is designed into the system. Dead volume is the non-compliant volume between the valve seats, that is the area between seats which defines the accumulator flow passage 86 and the non-compliant portion of the accumulator chamber 102. The valve seats are illustrated at the points 84. The dead volume between the valve seats 84 (not including the compliant accumulator volume which is nominally 1 $\mu$l) is in the range of 4.9–8.4$\mu$l. When closed, the accumulator 30 is isolated. When opened, the valves allow fluid communication to be established between the accumulator and the inlet conduit 54 or the outlet conduit 55.

Figure 5A:
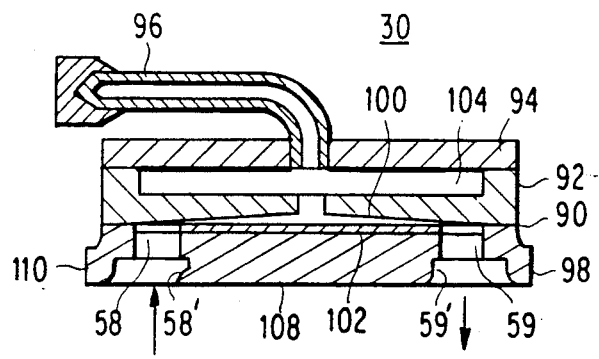
FIGS. 5A is a side view of the accumulator.
Figure 5B:
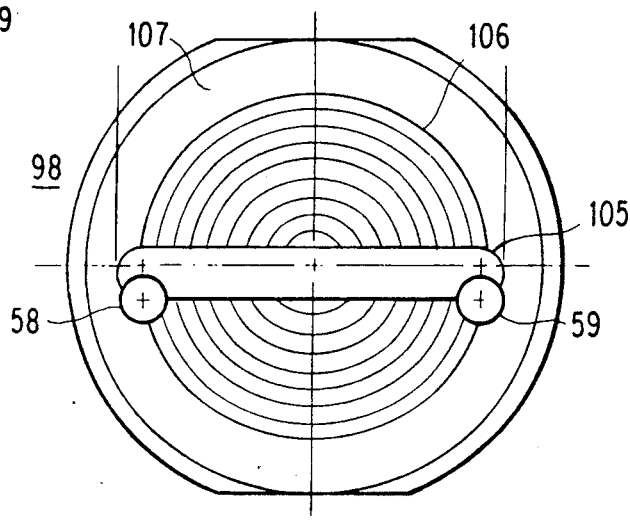
FIG. 5B is a top view of the spacer plate component of the accumulator in accordance with this invention.

Referring now to FIGS. 5A and 5B, details of the accumulator are depicted. The accumulator comprises a diaphragm 90, a backing plate 92, an end cap 94, a fill tube 96, and a spacer plate 98.

The accumulator and its diaphragm are a key component in this system. The diaphragm 90, as illustrated in FIG. 5A, is a circular disk of a thin metal sheet. Preferably titanium may be used. The disk is selected to have a diameter and thickness of virtually negligible spring rate over the desired range of deflection. Thus, the diaphragm acts as a compliant, flexible wall which separates fluid from the environment behind it.

The upward motion of the diaphragm 90 is limited by the backing plate 92. Backing plate 92 is a metal plug of the same material and diameter as that of the diaphragm 90. It is provided with a shallow concave profile manufactured into its lower surface. This surface 100 acts as a contour stop for the diaphragm 90. Dimensions of the contour are chosen to match the general profile of the diaphragm 90, when it is deflected by a predetermined fixed volume (e.g. 1 $\mu$l). This predetermined fixed volume is the volume desired to be metered, that is the volume of one discharge spike as illustrated in FIG. 2. Alternatively, the contour can be placed in the spacer plate 98.

The backing plate 92 acts as a mechanical stop which limits the motion of the diaphragm after the accumulator cavity 102 has been filled to a specified volume. The contour of the plate is designed so that it contacts as much of the surface of the diaphragm when the volume in chamber 102 has been reached. This surface on the backing plate 92 then rigidly stops all portions of the diaphragm from moving and for any further increase in pressure, the volume of the accumulator in zone 102 will not change. As long as the operating pressure of the pump is higher than the pressure required to fill the accumulator (to be discussed herein) the accumulator will then always store, in zone 102, the same volume irrespective of operating pressure variations. The ability to store and discharge the same volume repeatedly over a very large number of cycles irrespective of pump pressure, represents an important advantage over other implantable pumps in which the discharge rate is a function of the pressure generated by the twophase fluid. This is because pressure changes associated with two-phase fluid pumps are a function of pump temperature. If the user is in an environment where there is a significant temperature change at skin surface, for example during swimming, the pressure of the device will change.

The pressure differential across the diaphragm 90 determines whether it fills or empties. On the non-fluid side, the pressure effects both the fill and empty differentials. This pressure must be lower than the main reservoir pressure yet higher than the catheter outlet pressure. Consequently, the back fill pressure which exists on the side of the diaphragm 90 opposite that of the accumulator zone 102 must be controlled at a value which allows for complete filling yet guarantees complete emptying of the accumulator for any normal variations in reservoir or outlet pressure. Such a pressure can be chosen and maintained by controlling the pressure in chamber 104 and having it maintained in fluid communication with the backside of the diaphragm 90. The end cap 94 is used to cover this chamber. A fill tube 96 is used to charge the chamber 104 with an inert gas such as Argon maintained at 19.2 psia. The volume defined in the chamber 104 is chosen to be large enough so that any variations in the total volume due to diaphragm displacement will have negligible effect on the back fill pressure. Once chamber 104 has been filled with a pressurized gas, the fill tube 96 is sealed by welding. The tube 96 is chosen to have a small inside diameter so that changes in its length during welding or rework will not significantly effect the chamber volume and consequently, the backfill pressure.

FIG. 5B illustrates the details of the spacer plate 98. The spacer plate performs three major functions. First, it supports the diaphragm 90 during discharge. Secondly, it provides the annular passages as illustrated in FIG. 5B to enhance fluid flow. Thirdly it provides a technique for mounting the completed and tested units to the valve subassembly. In the same manner that the backing plate 92 supports the diaphragm during filling of the accumulator chamber 102, the spacer 98 is used to limit diaphragm motion during discharge. The spacer plate, however, need not be contoured because it supports the unstressed, that is the flat position of the diaphragm which is established during welding. The continuous contoured surface desirable to use as a mechanical stop on the gas-filled side of the diaphragm, that is in chamber 104 is undesirable on the fluid side. Intimate contact of two relatively flat surfaces with a liquid interface will create a suction effect which makes the separation of those surfaces difficult.

This suction effect can be overcome by the addition of a groove pattern having a series of concentric rings as illustrated in FIG. 5B. The prior art employed a series of orthogonal checkerboard grooves on the surface of the spacer plate. However, it was found that such a grid traps air bubbles in the cross grooves and small particles in the space between the gridded spacer plate and the diaphragm. This causes a shift in the pulse volume of the system. Importantly, it was found that the grid configuration had too much contact area with the diaphragm thus reducing the surface pressure. This resulted in the accumulation of precipitates such as insulin. The result was a reduction in the pulse volume. The spacer plate having a grid required a number of machine steps, such as turning and milling. It required chemical etching and therefore the overall cost of manufacture was high.

Given these problems with the existing configuration, the inventor considered a number of techniques as potential solutions. These included, steps in the spacer, a spiral cut, a porous insert, a "bed of nails" projecting up and the like. None were satisfactory. It was found however that by the use of a series of annular grooves, the problems of the prior art could be overcome. FIG. 5B illustrates the configuration of this invention.

The inlet 58 and outlet 59 are connected by means of a trough 105. A series of concentric circumferential grooves 106 are provided to establish fluid communication between the inlet 58 and the outlet 59. Also, the grooves are in fluid communication with the trough 105. The trough need not intersect with the inlet and outlet so long as together with a groove, fluid communication is established. Consequently, the spacer plate 98 defines flow paths comprising annular paths along grooves 106 and a direct lateral flow path along trough 105. The grooving is designed to permit complete free flow of fluid underneath the flattened diaphragm. Additionally, the grooves facilitate washing of areas because none of the grooves are at right angles to the flow path. Thus every groove experiences some degree of washing.

Dimensions of the grooves may be chosen to provide a minimum surface to support the diaphragm thereby increasing the contact pressure, that is the sharp ridges created between the adjacent grooves 106. This reduction in contact area prevents build up of drug residue and the potential entrapment of particles between the spacer plate and the diaphragm. At the same time this configuration maintains the accumulator dead volume at a minimum level. An annular grooved spacer plate also promotes the rapid filling and emptying of the accumulator zone 102 which in turn minimizes the time and therefore the energy necessary to hold either valve open. It can be appreciated that decreased valve energy requirements in such a system materially increase the life of the pump since the overall energy requirements of the system are decreased. Such as configuration can be made without chemical etching thus reducing manufacturing cost.

The top peripheral surface of the spacer plate 98 has a flat flange portion 107 devoid of any grooving to provide a clamping and sealing surface to the accumulator. The bottom of the spacer plate 98 as illustrated in FIG. 5A contains two counter bores 58 and 59 to mate with the valves which are illustrated in FIG. 4. The bottom surface 108 of the spacer plate 98 is controlled to be flat and have a smooth surface finish which will mate with the surface of the same quality on the valve subassembly. It is at this point that the weld 72 is made. Such again guarantees a minimum dead volume between parts and the minimum space for air entrapment.

The geometry of the outer flange 110 of the spacer plate matches the mating plate from the valves and permits a hermetic weld 72 around the rim. The spacer plate 98 outer flat annular portion 107 matches the shape of the backing plate 92 and provides a compression zone for sealing the unit.

Figure 6:
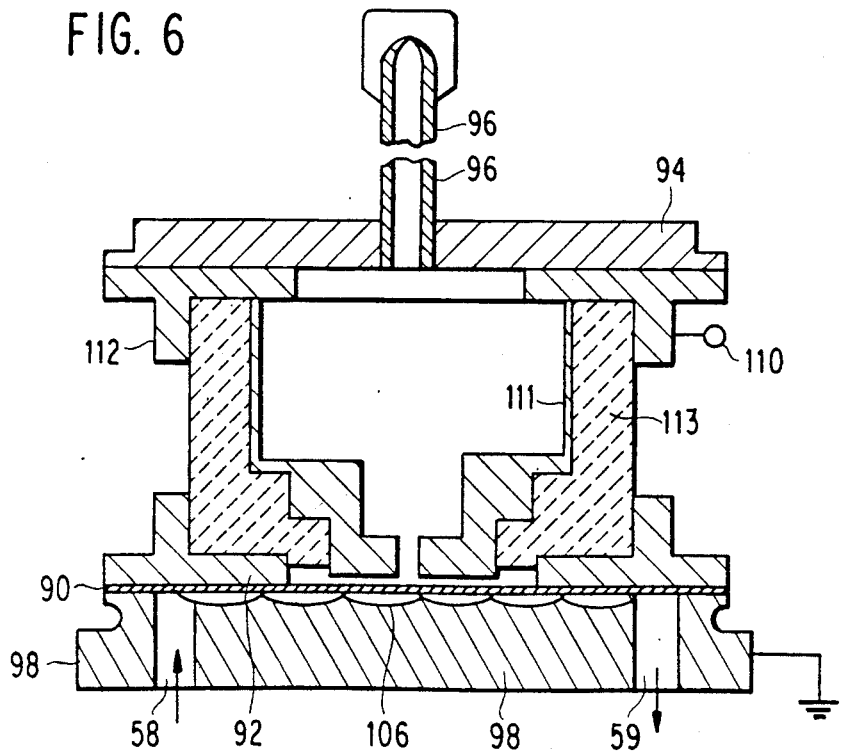
FIG. 6 is a cutaway side view of an electrical switch accumulator in accordance with this invention.

Referring now to FIG. 6, a modified accumulator is illustrated. This figure depicts a modification which employs the same basic elements of the accumulator as shown in FIGS. 5A and 5B. However, it employs an electrical switch to signal the level of volume within the accumulator. In accordance with this invention, by the use of the concentric groove spacer plate 98 electrical switching is facilitated. The switch plate surface is flat and the contour is thus cut into the groove spacer plate. The contour is easily formed by adjusting the depth or spacing of the grooves 106.

The dual functionality provided by the configuration of FIG. 6 is an important safety feature to indicate the presence of leaks in the valve seats and accumulator welds or, alternatively, sticking of the valves. Since this invention operates at positive pressure, failure of one or both valve seats may lead to improper dosing of the reservoir contents. A switch accumulator is thus important to sense conditions which are suggestive of valve misfunction and provide a warning signal to the operator to discontinue dosing.

The operating principles of the switch accumulator of FIG. 6 are identical to those of the accumulator illustrated in FIGS. 5A and 5B. However, as mentioned the contour is preferably moved to the spacer plate 98. The backing plate 92 can be manufactured flat. In FIG. 6, those elements which are common to the FIG. 5 configuration have like identification numbers. The backing plate 92 comprises three distinct elements which are used to electrically isolate the center of the plate from the diaphragm 90 and yet maintain the ability to store a sealed volume of inert gas. The end cap 94 and fill tube 96 have a dual function, that of chamber cover and electrical lead. The lead 110 is shown schematically attached to a flange 112 forming a portion of the end cap assembly. A ceramic assembly 113 is lined by a metallic portion 110 to provide a conductive path between the diaphragm and lead 110. The diaphragm is thus used as a moving switch contact.

That is, a full diaphragm will short the lead to the ground via the metalized ceramic 110 on the inside of the ceramic cup 113. Consequently, a signal is issued indicating that the accumulator is full, that is, the diaphragm in its upward position. This signal can be sensed by the system electronics just prior to opening or just following release of either valve. Consequently, by determining conditions during the sense period and by the switch state, a variety of diagnostic determinations can be made.

For example, during a sense period and just prior to the inlet opening, if an open switch condition exists, then the system is functioning properly. If, however, the switch state is closed then, it can be determined that there is a leak in the inlet valve 26. During the same period but just prior to pulsing the outlet, to release infusate from the accumulator, if an open switch exists, then a leak exists in the outlet valve seat or one of the valve or accumulator welds.

If, however, the switch of FIG. 6 is closed during the outlet sense period, the system is deemed to be functioning properly. Similarly, by sensing during the inlet portion of the cycle, but immediately following release, an open condition in the switch indicates that the inlet did not open or that there is a leak in the accumulator or valve weld. However, sensing the switch state as closed during the same period will indicate that the system is working acceptably. Consequently, by utilizing a switch accumulator of FIG. 6, a significant amount of information can be obtained concerning the status of the valve seats or the hermeticity of the metering system. By repeatedly pulsing the valve, failure mode can be determined to be repeatable or simply an artifact.

As can be seen by this invention then, the programmable pump operates at positive pressures and accurately controls the flow rate by metering discrete and repeatable volumes through a microaccumulator. The accumulator is filled and emptied by alternately cycling two control valves which are in series with the accumulator. Thus, by setting the cycling rate of the valves, the pump dispensing rate may be controlled.

The accumulator itself operates at a pressure which is intermediate between the pump reservoir pressure and the outlet pressure. This design pressure, when taken in conjunction with the negligible internal spring rate, guarantees a complete filling and emptying of the system. The volume, however, is repeatedly demonstrated, that is repeatedly dispensed and the valve energy requirements may be minimized. Given the design of the valves themselves, minimum dead volume and flow through occur. This minimizes the danger of entrapped air or stagnant flow in the system.

It is apparent that modifications of this design and of preferred embodiments therein may be made without departing from the essential scope of this invention.

Having described my invention. I claim:

1. An implantable infusion apparatus comprising:
a housing containing,
a rechargeable constant pressure infusate reservoir,
an electronically controlled metering assembly receiving infusate from said reservoir, said metering assembly comprising a pair of normally closed valves and an accumulator positioned in fluid communication with each of said valves, said accumulator comprising an inlet and outlet, a chamber having a diaphragm and a spacer plate, said spacer plate having a series of concentric grooves in fluid communication with said inlet and outlet,
electronic means for controlling the operation of said valves, and
outlet means in fluid communication with said metering assembly to dispense infusate to a site in a living body, wherein when a first of said valves is open, infusate flows from said reservoir into said accumulator chamber and into said concentric grooves, and when the other valve is open and the first closes, infusate flows from said accumulator into said outlet, said accumulator storing and discharging predetermined volume spikes of infusate at a frequency determined by the cycling rate of said pair of valves.

2. The device of claim 1, further comprising a bacteria/air filter arranged in said housing in a wall that separates said reservoir from the metering assembly.

3. The device of claim 1, wherein said housing further comprises a disk-shaped upper member, a hollow lower member and an internal base plate dividing the interior of the housing into two chambers, a solid central core disposed on said base plate and said disk-shaped upper member said central core comprising a septum for refilling said reservoir.

4. The device of claim 3, further comprising a needle-stop and an inlet check valve disposed in the central core.

5. The device of claim 1, wherein said pair of valves are positioned side-by-side in fluid isolation, each of said valves having a conduit to said accumulator that may be opened or closed by a valve member and, said accumulator positioned on both of said valves, said accumulator having said inlet aligned with one of said conduits and said outlet aligned with the other of said conduits.

6. The device of claim 1, wherein said accumulator further comprises an end cap, a backing plate, and said spacer plate has a straight groove connecting said inlet and said outlet, said diaphragm positioned between said backing plate and said spacer plate.

7. The device of claim 6 wherein said backing plate contains a recess, said recess covered by said end cap, means to fill said recess with a fluid under pressure and means in said backing plate to establish fluid communication between said recess and one side of said diaphragm.

8. The device of claim 6, wherein contoured surface defines a stop for said diaphragm when said accumulator has been filled with infusate, said contoured surface contacting substantially the entire surface of said diaphragm to limit any change in the stored volume of the accumulator irrespective of changes in pressure of infusate delivered from the reservoir.

9. The device of claim 6, wherein said spacer plate concentric grooves are separated by sharp projecting edges, said projecting edges contacting and supporting said diaphragm when said accumulator is emptied.

10. The device of claim 9, wherein said spacer plate straight groove is in fluid communication with said concentric grooves.

11. The device of claim 6 said backing plate further comprising a conductive inner surface, an insulator isolating said backing plate and, electrical means providing an output to determine the position of said diaphragm.

12. The device of claim 6, said spacer plate further comprising an outer flat annular surface for sealing said spacer plate within said accumulator.

13. The device of claim 1, further comprising programmer means external to said housing for interrogating and programming said electronic means.

14. The device of claim 1, wherein said outlet means comprises a catheter attached to said housing, said outlet catheter including a connector insertable into said outlet port.

15. The device of claim 1, further comprising a side-port for the direct injection of a drug into said outlet.

16. An implantable infusion apparatus comprising:
a sealed housing having an inlet septum,
a rechargeable constant pressure infusate reservoir in said housing,
metering means in said housing receiving infusate from said reservoir, said metering means comprising first and second valves and a fixed volume accumulator positioned in fluid communication with each of said valves, said accumulator comprising an inlet and an outlet, a chamber, a diaphragm and spacer plate in said chamber, said spacer plate having a series of concentric grooves in fluid communication with said inlet and outlet,
electronic means in said housing for controlling the operation of said valves, such that when a first of said valves is open, infusate flows from said reservoir into said accumulator to fill said accumulator by deflection of said diaphragm and when the second valve is open and the first valve closes, infusate flows from said accumulator and, outlet means in fluid communication with said metering means to dispense infusate to a site in a living body, whereby infusate dispensed in a series of predetermined volume spikes, the frequency of said spikes determined by the cycling rate of said first and second valves.

17. The device of claim 16, further comprising filter means arranged in said sealed housing in a wall that separates said reservoir from said metering means.

18. The device of claim 16, wherein said sealed housing comprises a disk-shaped upper member, a hollow lower member and an internal baseplate dividing the interior of the housing into two chambers, a solid central core disposed on said baseplate and said disk-shaped upper member, said central core positioning said septum for refilling said reservoir, and further comprising a needle-stop disposed below said septum and an inlet check valve disposed below said needle-stop.

19. The device of claim 16, wherein said first and second valves are positioned side-by-side in fluid isolation with each other, each of said valves having a conduit to said accumulator that may be opened or closed by a valve member and, said accumulator having said inlet aligned with one of said conduits and said outlet aligned with the other of said conduits.

20. The device of claim 16, wherein said accumulator comprises an end cap, a backing plate, an inextensible diaphragm, and said spacer plate having a straight groove in fluid communication between said inlet and said outlet said diaphragm sandwiched between said backing plate and said spacer plate.

21. The device of claim 20, wherein said backing plate contains a recess, said recess covered by said end cap, means to fill said recess with a fluid under pressure and conduit means in said backing plate to establish fluid communication between said recess and one side of said diaphragm to bias said diaphragm.

22. The device of claim 20, wherein said contoured surface defines a stop for said diaphragm when said accumulator has been filled with infusate whereby said contoured surface contacting substantially the entire surface of said diaphragm to limit any change in the stored volume of the accumulator irrespective of changes in pressure of infusate delivered from the reservoir to said accumulator.

23. The device of claim 22, wherein said spacer plate concentric grooves are separated by a series of sharp projecting walls supporting said diaphragm.

24. The device of claim 23, wherein said spacer plate concentric grooves are in fluid communication with said straight groove.

25. The device of claim 20 wherein said backing plate comprises a conductive inner surface, an insulator isolating said backing plate from said spacer plate and, electrical means providing an output to determine the position of said diaphragm.

26. The device of claim 16, further comprising programmer means external to said housing for interrogating and programming said electronic means.

27. The device of claim 16, wherein said outlet means comprises an outlet catheter attached to said housing, said outlet catheter including a connector lockably insertable into said outlet port.

28. The device of claim 16, further comprising a side-port for the direct injection of a drug into said outlet.

* * * * *